United States Patent
Eckhardt et al.

(10) Patent No.: US 7,687,469 B2
(45) Date of Patent: *Mar. 30, 2010

(54) GLUCOPYRANOSYL-SUBSTITUTED BENZENE DERIVATIVES, MEDICAMENTS CONTAINING SUCH COMPOUNDS, THEIR USE AND PROCESS FOR THEIR MANUFACTURE

(75) Inventors: Matthias Eckhardt, Biberach (DE); Frank Himmelsbach, Mittelbiberach (DE); Peter Eickelmann, Mittelbiberach (DE); Leo Thomas, Biberach (DE); Edward Leon Barsoumian, Toyonaka (JP)

(73) Assignee: Boehringer Ingelheim International GmbH, Ingelheim (DE)

(*) Notice: Subject to any disclaimer, the term of this patent is extended or adjusted under 35 U.S.C. 154(b) by 219 days.

This patent is subject to a terminal disclaimer.

(21) Appl. No.: 11/304,284

(22) Filed: Dec. 15, 2005

(65) Prior Publication Data

US 2006/0142210 A1 Jun. 29, 2006

(30) Foreign Application Priority Data

Dec. 16, 2004 (DE) .......................... 10 2004 061 145
Feb. 9, 2005 (EP) ............................... 05 002 628

(51) Int. Cl.
*A61K 31/7004* (2006.01)
*C07H 7/04* (2006.01)
(52) U.S. Cl. ........................................ 514/23; 536/1.11
(58) Field of Classification Search ........................ None
See application file for complete search history.

(56) References Cited

U.S. PATENT DOCUMENTS

| | | | |
|---|---|---|---|
| 4,602,023 A | 7/1986 | Kiely et al. |
| 4,786,755 A | 11/1988 | Kiely et al. |
| 6,414,126 B1 | 7/2002 | Ellsworth et al. |
| 6,515,117 B2 | 2/2003 | Ellsworth et al. |
| 6,627,611 B2 | 9/2003 | Tomiyama et al. |
| 6,774,112 B2 | 8/2004 | Gougoutas |
| 6,936,590 B2 | 8/2005 | Washburn et al. |
| 7,169,761 B2 | 1/2007 | Tomiyama et al. |
| 7,202,350 B2 | 4/2007 | Imamura et al. |
| 7,371,732 B2 | 5/2008 | Eickelmann et al. |
| 7,375,090 B2 | 5/2008 | Himmelsbach et al. |
| 7,393,836 B2 | 7/2008 | Eckhardt et al. |
| 7,417,032 B2 | 8/2008 | Eckhardt et al. |
| 7,419,959 B2 | 9/2008 | Eckhardt et al. |
| 7,579,449 B2 | 8/2009 | Eckhardt et al. |
| 2002/0137903 A1 | 9/2002 | Ellsworth et al. |
| 2003/0064935 A1 | 4/2003 | Gougoutas |
| 2003/0114390 A1 | 6/2003 | Washburn et al. |
| 2004/0138148 A1 | 7/2004 | Fushimi et al. |
| 2004/0138439 A1 | 7/2004 | Deshpande et al. |
| 2005/0065098 A1 | 3/2005 | Fujikura et al. |
| 2005/0124555 A1 | 6/2005 | Tomiyama et al. |
| 2005/0209166 A1* | 9/2005 | Eckhardt et al. .............. 514/23 |
| 2006/0009400 A1 | 1/2006 | Eckhardt et al. |
| 2006/0019948 A1 | 1/2006 | Eckhardt et al. |
| 2006/0025349 A1 | 2/2006 | Eckhardt et al. |
| 2006/0035841 A1 | 2/2006 | Eckhardt et al. |
| 2006/0063722 A1 | 3/2006 | Washburn et al. |
| 2006/0074031 A1 | 4/2006 | Eckhardt et al. |
| 2006/0142210 A1 | 6/2006 | Eckhardt et al. |
| 2006/0189548 A1 | 8/2006 | Himmelsbach et al. |
| 2006/0234953 A1 | 10/2006 | Himmelsbach et al. |
| 2006/0251728 A1 | 11/2006 | Himmelsbach et al. |
| 2006/0258749 A1 | 11/2006 | Eckhardt et al. |
| 2007/0004648 A1 | 1/2007 | Himmelsbach et al. |
| 2007/0027092 A1 | 2/2007 | Himmelsbach et al. |
| 2007/0049537 A1 | 3/2007 | Eckhardt et al. |
| 2007/0054867 A1 | 3/2007 | Eckhardt et al. |
| 2007/0073046 A1 | 3/2007 | Eckhardt et al. |
| 2007/0249544 A1 | 10/2007 | Himmelsbach et al. |
| 2007/0259821 A1 | 11/2007 | Eckhardt et al. |
| 2008/0058379 A1 | 3/2008 | Eckhardt et al. |
| 2009/0023913 A1 | 1/2009 | Eckhardt et al. |

FOREIGN PATENT DOCUMENTS

| | | | |
|---|---|---|---|
| CA | 2 388 818 A1 | 4/2001 |
| CA | 2 494 177 A1 | 2/2004 |
| CA | 2 508 024 A1 | 6/2004 |
| CA | 2 508 226 A1 | 6/2004 |
| CA | 2 526 145 A1 | 9/2004 |
| CA | 2 557 269 A1 | 9/2005 |
| CA | 2 557 320 A1 | 9/2005 |
| CA | 2 557 801 A1 | 10/2005 |

(Continued)

OTHER PUBLICATIONS

International Search Report for corresponding international application PCT/EP2005/056806 mailed Dec. 27, 2006.
International Search Report for PCT/EP2005/002618 mailed Jun. 30, 2005.
Nouri Neamati et al; Depsides and Depsidones as inhibitors of HIV-1 Integrase: Discovery of Novel Inhibitors Through 3D Database Searching; Journal Medicinal Chemistry (1997) vol. 40 pp. 942-951.
Tetsuya Adachi et al; T-1095, A Renal Na+-Glucose Transporter Inhibitor, Improves Hyperglycemia in Streptozotocin-Induced Diabetic Rats; Metabolism (2001) vol. 49 No. 8 pp. 990-995.
Takehiko Iida et al; TributyImagnesium Ate Complex-Mediated Novel Bromine-Magnesium Exchange Reaction for Selective Monosubstitution of Dibromoarenes; Tetrahedron Letters (2001) vol. 42 pp. 4841-4844; Pergamon Press.

(Continued)

*Primary Examiner*—Shaojia Anna Jiang
*Assistant Examiner*—Eric S Olson
(74) *Attorney, Agent, or Firm*—Michael P. Morris; Edouard G. Lebel; David A. Dow

(57) ABSTRACT

Glucopyranosyl-substituted benzene derivatives defined according to claim 1, including the tautomers, the stereoisomers thereof, the mixtures thereof and the salts thereof. The compounds according to the invention are suitable for the treatment of metabolic disorders.

8 Claims, No Drawings

FOREIGN PATENT DOCUMENTS

| | | |
|---|---|---|
| CA | 2 573 777 A1 | 2/2006 |
| EP | 0 206 567 A2 | 6/1986 |
| EP | 1344780 A1 | 9/2003 |
| EP | 1 385 856 A0 | 2/2004 |
| EP | 1 224 195 B1 | 5/2005 |
| EP | 1 553 094 A1 | 7/2005 |
| EP | 1 609 785 A1 | 12/2005 |
| JP | 58-164502 A | 9/1983 |
| JP | 62-30750 A | 2/1987 |
| JP | 11/124392 A | 5/1999 |
| JP | 2001/288178 A | 10/2001 |
| JP | 2003-511458 A | 3/2003 |
| JP | 2004-359630 A | 12/2004 |
| WO | 98/31697 A1 | 7/1998 |
| WO | 01/27128 A1 | 4/2001 |
| WO | 01/74834 A1 | 10/2001 |
| WO | 02/064606 A1 | 8/2002 |
| WO | 02/083066 A2 | 10/2002 |
| WO | 03/099836 A1 | 12/2003 |
| WO | 2004/013118 A1 | 2/2004 |
| WO | 2004/052902 A1 | 6/2004 |
| WO | 2004/052903 A1 | 6/2004 |
| WO | 2004/063209 A2 | 7/2004 |
| WO | 2004/076470 A2 | 9/2004 |
| WO | 2004/080990 A1 | 9/2004 |
| WO | 2005/012318 A2 | 2/2005 |
| WO | 2005/012326 A1 | 2/2005 |
| WO | 2005/085237 A1 | 9/2005 |
| WO | 2005/085265 A1 | 9/2005 |
| WO | 2005/092877 A1 | 10/2005 |
| WO | 2006/011469 A1 | 2/2006 |
| WO | 2006/034489 A2 | 3/2006 |
| WO | 2006/064033 A2 | 6/2006 |
| WO | 2006/089872 A1 | 8/2006 |
| WO | 2006/108842 A1 | 10/2006 |
| WO | 2006/117360 A1 | 11/2006 |
| WO | 2006/120208 A1 | 11/2006 |
| WO | 2007/014894 A2 | 2/2007 |
| WO | 2007/025943 A2 | 3/2007 |
| WO | 2007/028814 A1 | 3/2007 |
| WO | 2007/031548 A2 | 3/2007 |

OTHER PUBLICATIONS

Craig A Hutton et al; A Convenient Preparation of dityrosine Via Miyaura Borylation-Suzuki Coupling of Iodotyrosine Derivatives; Tetrahedron Letters (2003) vol. 44 pp. 4895-4898; Pergamon Press.

Alois Fuerstner et al; Practical Method for the Rhodium-Catalyzed Addition of Aryl- and Alkenylboronic Acids to Aldehydes; Advanced Synthesis and Catalysis (2001) vol. 343 No. 4 pp. 343-350.

Wolfgang Dohle et al; Copper-Mediated Cross-Coupling of Functionalized Arylmagnesium Reagents with Functionalized Alkyl and Benzylic Halides; Organic Letters (2001) vol. 3 No. 18 pp. 2871-2873.

Sabrina M. Norbre et al; Synthesis of Diarylmethane Derivatives from Pd-Catalyzed Cross-Coupling Reactions of Benzylic Halides with Arylboronic Acids; Tetrahedron Letters (2004) vol. 45 8225-8228.

Mark McLaughlin et al; Suzuki-Miyaura Cross-Coupling of Benzylic Phosphahates with Arylboronic Acids; Organic Letters (2005) vol. 7 No. 22 pp. 4875-4878.

Masanori Hatsuda et al; A Practical Synthesis of Highly Functionalized Aryl Nitriles Through Cyanation of Aryl Bromides Employing Heterogeneous Pd/C; Tetrahedron Letters (2005) vol. 46 pp. 1849-1853; Elsevier Ltd.

Federica Stazi et al; Statistical Experimental Design-Driven Discovery of room-Temperature Conditions for Palladium-Catalyzed Cyanation of Aryl Bromides; Tetrahedron Letters (2005) vol. 46 1815-1818; Elsevier Ltd.

Ja Seo Koo et al; 2-Pyridyl Cyanate: A Useful Reagent for he Preparation of Nitriles; Synthetic Communications (1996) vol. 26 No. 20 pp. 3709-3713; Marcel Dekker, Inc.

Michael Bech Sommer et al; displacement of Halogen of 2-Halogeno-Substituted Benzonitriles with Carbonions. Preparation of (2-Cyanoaryl)arylacetonitriles; Journal of Organic Chemistry (1990) vol. 55 pp. 4817-4821.

Richard J. Perner et al; 5,6,7-Trisubstituted 4-Aminopyrido[2,3-d]pyrimidines as Novel inhibitors of Adenosime Kinase; Journal of Medicinal Chemistry (2003) vol. 46 pp. 5249-5257.

Debra J. Wallace et al; Cyclopropylboronic Acid: Synthesis and Suzuki Cross-Coupling Reactions; Tetrahedron Letters (2002) vol. 43 pp. 6987-6990; Pergamon Press.

Sandrine Langle et al; Selective Double Suzuki Cross-Coupling Reactions. Synthesis of Unsymmetrical Diaryl (or Heteroaryl) Methanes; Tetrahedron Letters (2003) vol. 44 pp. 9255-9258; Pergamon Press.

International Search Report for PCT/EP2007/051411 mailed on May 2, 2007.

International Search Report for PCT/EP2007/054248 mailed on Jun. 18, 2007.

Rik R. Tykwinski; Evolution in the Palladium-Catalyzed Cross-Coupling of sp- and sp2-Hybridized Carbon Atoms; Angew Chemical International Edition (2003) vol. 42 pp. 1566-1568.

G. Erik Jagdmann, Jr; Synthesis of 5-(4-Substituted Benzyl)-2,4-Diaminoquinazolines as Inhibitors of Candida Albicans Dihydrofolate Reductase; Journal Heterocyclic Chemical (1995) vol. 32 pp. 1461-1465.

International Search Report for PCT/EP2006/061956 mailed on Jul. 5, 2006.

Lasslo Revesz et al; SAR of Benzoylpylpyridines and Benzophenones as p38 Alpha MAP Kinase Inhibitors with Oral Activity; Bioorganic & Medicinal Chemistry Letters (2004) vol. 14 pp. 3601-3605.

International Search Report for PCT/EP2006/062191 mailed Aug. 8, 2006.

International Search Report for PCT/EP2006/066107 mailed Jan. 11, 2007.

International Search Report for PCT/EP2006/066347 mailed Mar. 7, 2007.

Song Xue et al; Zinc-mediated Synthesis of Alpha-C-Glycosided from 1,2-Anhydroglycosides; Synletters (2003) vol. 6 pp. 870-872.

Takeshi Kuribayashi et al; Bis C-Glycosylated Diphenylmethanes for Stable Glycoepitope Mimetics; Syntletters (1999) vol. 6 pp. 737-740.

International Search Report for PCT/EP2006/065710 mailed Mar. 8, 2007.

U.S. Appl. No. 11/674,839, filed Feb. 14, 2007.

U.S. Appl. No. 11/742,612, filed May 1, 2007.

International Search Report for PCT/EP2006/061957 mailed on Jul. 5, 2006.

Takeshi Kuribayashi, et al; c-Glycosylated Aryl tins: Versatile Building Blocks for Aryl C-Glycoside Glycomimetics; J. Carbohydrate Chemistry (1999) vol. 18, No. 4 pp. 371-382.

Takeshi Kuribayashi, et al; C-Glycosylated Diphenylmethanes and Benzophenones: The Stille Coupling Reaction of C-Glycosylated Aryl tins with Benzyl Bromides and Acid Chlorides; J. Carbohydrate Chemistry (1999) vol. 18, No. 4 pp. 393-401.

Noui Neamati, et al, "Depsides and Depsidones as Inhibiton of HIV-1 Integrase: Dimvery of Novel Inhibitors Through 3D Database Searclung", J. Med. Chem., 1997, vol. 40, pp. 942-951.

Akira Oku, et al; T-1095, An Inhibitor or renal $Na^+$—Glucose Cotransporters, May Provide a Novel Approach to Treating Diabetes; Diabetes (1999) vol. 48 pp. 1794-1800.

Kiichiro Ueta, et al; Long-Term Treatment with the $Na^+$—Glucose Cotransporter Inhibitor T-1095 Causes Sustained Improvement in Hyperglycemia and Prevents Diabetic Neuropathy in Goto-Kakizaki Rats; Life Sciences (2005) vol. 76 pp. 2655-2668.

International Search Report for PCT/EP2006/061520 mailed Jul. 26, 2006.

International Search Report for PCT/EP2006/064702 mailed on Jul. 26, 2007.

Non-Final Office Action dated Jun. 24, 2008 from U.S. Appl. No 11/406,971, filed Apr. 19, 2006.

Non-Final Office Action dated Jun. 5, 2008 from U.S. Appl. No. 11/408,899, filed on Apr. 21, 2006.
Non Final Office Action dated Apr. 2, 2008 from U.S. Appl. No. 11/674,839, filed on Feb. 14, 2007.
Response to Non-Final Office Action dated Apr. 2, 2008 from U.S. Appl. No. 11/674,839, filed Feb. 14, 2007.
Non Final Office Action dated Apr. 2, 2008 from U.S. Appl. No. 11/742,612, filed on May 1, 2007.
Response to Non-Final Office Action dated Apr. 2, 2008 from U.S. Appl. No. 11/742,612, filed May 1, 2007.
Rachida Benhaddou et al; Tetra-n-Propylammonium Tetra-Oxoruthenate(VII): A Reagent of Choice for the Oxidation of Diversely Protected Glycopyranoses and Glycofuranoses to Lactones; Carbohydrate Research (1994) vol. 260 pp. 243-250.
Non-Final Office Action dated May 8, 2008 from U.S. Appl. No. 11/359,846 filed February 22, 2006.
Response dated November 5, 2008 to Non-Final Office Action dated May 8, 2008 from U.S. Appl. No. 11/359,846 filed February 22, 2006.
Notice of Allowance and Fee(s) Due dated February 3, 2009 from U.S. Appl. No. 11/359,846 filed February 22, 2006.
Notice of Allowance and Fee(s) Due dated December 30, 2008 from U.S. Appl. No. 11/674,839 filed February 14, 2007.
Notice of Allowance and Fee(s) Due dated January 2, 2009 from U.S. Appl. No. 11/742,612 filed May 1, 2007.
U.S. Appl. No. 12/545,175, filed Aug. 21, 2009.

* cited by examiner ns-1-yl)-benzene,

GLUCOPYRANOSYL-SUBSTITUTED BENZENE DERIVATIVES, MEDICAMENTS CONTAINING SUCH COMPOUNDS, THEIR USE AND PROCESS FOR THEIR MANUFACTURE

This application claims priority to German application DE 10 2004 061 145.9, filed Dec. 16, 2004, and European Application EP 05 002 628.5, filed Feb. 9, 2005.

The present invention relates to new glucopyranosyl-substituted benzene derivatives or derivatives thereof, including the tautomers, the stereoisomers thereof or the mixtures thereof, and the salts thereof. The invention further relates to pharmaceutical compositions containing a compound according to the invention as well as the use of a compound according to the invention for preparing a pharmaceutical composition for the treatment of metabolic disorders. In addition, the invention relates to processes for preparing a pharmaceutical composition as well as a compound according to the invention.

In the literature, compounds which have an inhibitory effect on the sodium-dependent glucose cotransporter SGLT2 are proposed for the treatment of diseases, particularly diabetes.

Glucopyranosyloxy-substituted aromatic groups and the preparation thereof and their possible activity as SGLT2 inhibitors are known from published International applications WO 98/31697, WO 01/27128, WO 02/083066, WO 03/099836, WO 2004/063209, WO 2004/080990, WO 2004/013118, WO 2004/052902, WO 2004/052903, US application US 2003/0114390 and WO 2005/092877.

Aim of the Invention

The aim of the present invention is to find new pyranosyloxy-substituted benzene derivatives, particularly those which are active with regard to the sodium-dependent glucose cotransporter SGLT, particularly SGLT2. A further aim of the present invention is to discover pyranosyloxy-substituted benzene derivatives which have an enhanced inhibitory effect on the sodium-dependent glucose cotransporter SGLT2 in vitro and/or in vivo compared with known, structurally similar compounds and/or have better pharmacological or pharmacokinetic properties.

A further aim of the present invention is to provide new pharmaceutical compositions which are suitable for the prevention and/or treatment of metabolic disorders, particularly diabetes.

Other aims of the present invention will become apparent to the skilled man directly from the foregoing and following remarks.

OBJECT OF THE INVENTION

In a first aspect the present invention relates to glucopyranosyl-substituted benzene derivatives selected from the group consisting of
(1) 1-Methyl-2-(4-cyclopentyloxy-benzyl)-4-(β-D-glucopyranos-1-yl)-benzene,
(2) 1-Methyl-2-[4-((R)-tetrahydrofuran-3-yloxy)-benzyl]-4-(β-D-glucopyranos-1-yl)-benzene,
(3) 1-Methyl-2-[4-((S)-tetrahydrofuran-3-yloxy)-benzyl]-4-(β-D-glucopyranos-1-yl)-benzene,
(4) 1-Methyl-2-(4-cyclohexyloxy-benzyl)-4-(β-D-glucopyranos-1-yl)-benzene,
(5) 1-Chloro-2-[4-(1-tert-butyloxycarbonylpiperidin-4-yloxy)-benzyl]-4-(β-D-glucopyranos-1-yl)-benzene,
(6) 1-Chloro-2-[4-(piperdin-4-yloxy)-benzyl]-4-(β-D-glucopyranos-1-yl)-benzene,
(7) 1-Methoxy-2-(β-D-glucopyranos1-yl)-4-(4-ethynyl-benzyl)-benzene,
(8) 1-Chloro-2-(4-methoxymethylethynyl-benzyl)-4-(β-D-glucopyranos-1-yl)-benzene,
(9) 1-Chloro-2-(4-hydroxymethylethynyl-benzyl)-4-(β-D-glucopyranos-1-yl)-benzene,
(10) 1-Chloro-2-(4-hydroxyethylethynyl-benzyl)-4-(β-D-glucopyranos-1-yl)-benzene,
(11) 1-Ethynyl-2-(4-methoxy-benzyl)-4-(β-D-glucopyranos-1-yl)-benzene,
(12) 1-Methyl-2-(4-butyn-1-yl-benzyl)-4-(β-D-glucopyranos-1-yl)-benzene,
(13) 1-Chloro-2-(4-propyn-1-yl-benzyl)-4-(β-D-glucopyranos-1-yl)-benzene,
(14) 1-Methyl-2-(4-propyn-1-yl-benzyl)-4-(β-D-glucopyranos-1-yl)-benzene,
(15) 1-Isopropyl-2-(4-ethynyl-benzyl)-4-(β-D-glucopyranos-1-yl)-benzene,
(16) 1-Chloro-2-(4-isopropylethynyl-benzyl)-4-(β-D-glucopyranos-1-yl)-benzene, or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenylcarbonyl, phenyl-($C_{1-3}$-alkyl)-carbonyl and phenylcarbonyl, or a pharmaceutically acceptable salt thereof; including the tautomers, the stereoisomers thereof, the mixtures thereof, and salts thereof The compounds according to the invention and the physiologically acceptable salts thereof have valuable pharmacological properties, particularly an inhibitory effect on the sodium-dependent glucose cotransporter SGLT, particularly SGLT2. Moreover compounds according to the invention may have an inhibitory effect on the sodium-dependent glucose cotransporter SGLT1. Compared with a possible inhibitory effect on SGLT1 the compounds according to the invention preferably inhibit SGLT2 selectively.

The present invention also relates to the physiologically acceptable salts of the compounds according to the invention with inorganic or organic acids.

This invention also relates to pharmaceutical compositions, containing at least one compound according to the invention or a physiologically acceptable salt according to the invention, optionally together with one or more inert carriers and/or diluents.

This invention also relates to the use of at least one compound according to the invention or one of the physiologically acceptable salts thereof for preparing a pharmaceutical composition which is suitable for the treatment or prevention of diseases or conditions which can be influenced by inhibiting the sodium-dependent glucose cotransporter SGLT, particularly SGLT2.

This invention also relates to the use of at least one compound according to the invention or one of the physiologically acceptable salts thereof for preparing a pharmaceutical composition which is suitable for the treatment of one or more metabolic disorders.

This invention also relates to the use of at least one compound according to the invention or one of the physiologically acceptable salts thereof for preparing a pharmaceutical composition for inhibiting the sodium-dependent glucose cotransporter SGLT, particularly SGLT2.

DETAILED DESCRIPTION OF THE INVENTION

The aspects according to the present invention, in particular the compounds, pharmaceutical compositions and uses thereof, refer to glucopyranosyl-substituted benzene derivatives selected from the group of compounds (1) to (16) as defined hereinbefore and hereinafter, or derivatives thereof, including tautomers, stereoisomers or mixtures thereof, or physiologically acceptable salts thereof.

Preferably all hydroxyl groups of the β-D-glucopyranosyl group are not substituted or only the hydroxyl group O-6 of the β-D-glucopyranosyl group is substituted as defined. Preferred substituents are selected from among ($C_{1-8}$-alkyl)carbonyl, ($C_{1-8}$-alkyl)oxycarbonyl and phenylcarbonyl. Even more preferred substituents are selected from among acetyl, methoxycarbonyl and ethoxycarbonyl, in particular ethoxycarbonyl.

The compounds according to the invention may be obtained using methods of synthesis known in principle. Preferably the compounds are obtained by the methods as described and/or cited in the WO 2005/092877. In addition suitable methods of synthesis may be adapted from the literature, for example the methods described in WO 98/31697, WO 01/27128, WO 02/083066, WO 03/099836 and WO 2004/063209.

The compounds according to this invention may be resolved into their enantiomers and/or diastereomers. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds according to this invention obtained which occur as racemates may be separated by methods known per se (cf. Allinger N. L. and Eliel E. L. in "Topics in Stereochemistry", Vol. 6, Wiley Interscience, 1971) into their optical antipodes and compounds according to this invention with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)-or (−)-menthyloxycarbonyl.

Furthermore, the compounds according to this invention may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, the compounds obtained may be converted into mixtures, for example 1:1 or 1:2 mixtures with amino acids, particularly with alpha-amino acids such as proline or phenylalanine, which may have particularly favourable properties such as a high crystallinity.

As already mentioned, the compounds according to this invention and the physiologically acceptable salts thereof have valuable pharmacological properties, particularly an inhibitory effect on the sodium-dependent glucose cotransporter SGLT, preferably SGLT2.

The biological properties of the new compounds may be investigated as follows:

The ability of the substances to inhibit the SGLT-2 activity may be demonstrated in a test set-up in which a CHO-K1 cell line (ATCC No. CCL 61) or alternatively an HEK293 cell line (ATCC No. CRL-1573), which is stably transfected with an expression vector pZeoSV (Invitrogen, EMBL accession number L36849), which contains the cDNA for the coding sequence of the human sodium glucose cotransporter 2 (Genbank Acc. No. NM_003041) (CHO-h SGLT2 or HEK-hS-GLT2). These cell lines transport $^{14}$C-labelled alpha-methylglucopyranoside ($^{14}$C-AMG, Amersham) into the interior of the cell in sodium-dependent manner.

The SGLT-2 assay is carried out as follows:

CHO-hSGLT2 cells are cultivated in Ham's F12 Medium (BioWhittaker) with 10% foetal calf serum and 250 µg/ml zeocin (Invitrogen), and HEK293-hSGLT2 cells are cultivated in DMEM medium with 10% foetal calf serum and 250 µg/ml zeocin (Invitrogen). The cells are detached from the culture flasks by washing twice with PBS and subsequently treating with trypsin/EDTA. After the addition of cell culture medium the cells are centrifuged, resuspended in culture medium and counted in a Casy cell counter. Then 40,000 cells per well are seeded into a white, 96-well plate coated with poly-D-lysine and incubated overnight at 37° C., 5% $CO_2$. The cells are washed twice with 250 µl of assay buffer (Hanks Balanced Salt Solution, 137 mM NaCl, 5.4 mM KCl, 2.8 mM $CaCl_2$, 1.2 mM $MgSO_4$ and 10 mM HEPES (pH7.4), 50 µg/ml of gentamycin). 250 µl of assay buffer and 5 µl of test compound are then added to each well and the plate is incubated for a further 15 minutes in the incubator. 5 µl of 10% DMSO are used as the negative control. The reaction is started by adding 5 µl of $^{14}$C-AMG (0.05 µCi) to each well. After 2 hours' incubation at 37° C., 5% $CO_2$, the cells are washed again with 250 µl of PBS (20° C.) and then lysed by the addition of 25 µl of 0.1 N NaOH (5 min. at 37° C.). 200 µl of MicroScint20 (Packard) are added to each well and incubation is continued for a further 20 min at 37° C. After this incubation the radioactivity of the $^{14}$C-AMG absorbed is measured in a Topcount (Packard) using a $^{14}$C scintillation program.

To determine the selectivity with respect to human SGLT1 an analogous test is set up in which the cDNA for hSGLT1 (Genbank Acc. No. NM000343) instead of hSGLT2 cDNA is expressed in CHO-K1 or HEK293 cells.

The compounds according to the invention may for example have EC50 values below 1000 nM, particularly below 200 nM, most preferably below 50 nM.

In view of their ability to inhibit the SGLT activity, the compounds according to the invention and the corresponding physiologically acceptable salts thereof are theoretically suitable for the treatment and/or preventative treatment of all those conditions or diseases which may be affected by the inhibition of the SGLT activity, particularly the SGLT-2 activity. Therefore, compounds according to the invention are particularly suitable for the prevention or treatment of diseases, particularly metabolic disorders, or conditions such as type 1 and type 2 diabetes mellitus, complications of diabetes (such as e.g. retinopathy, nephropathy or neuropathies, diabetic foot, ulcers, macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

These substances are also suitable for preventing beta-cell degeneration such as e.g. apoptosis or necrosis of pancreatic beta cells. The substances are also suitable for improving or restoring the functionality of pancreatic cells, and also of increasing the number and size of pancreatic beta cells. The compounds according to the invention may also be used as diuretics or antihypertensives and are suitable for the prevention and treatment of acute renal failure.

In particular, the compounds according to the invention, including the physiologically acceptable salts thereof, are suitable for the prevention or treatment of diabetes, particularly type 1 and type 2 diabetes mellitus, and/or diabetic complications.

The dosage required to achieve the corresponding activity for treatment or prevention usually depends on the compound which is to be administered, the patient, the nature and gravity of the illness or condition and the method and frequency of administration and is for the patient's doctor to decide. Expediently, the dosage may be from 1 to 100 mg, preferably 1 to 30 mg, by intravenous route, and 1 to 1000 mg, preferably 1 to 100 mg, by oral route, in each case administered 1 to 4 times a day. For this purpose, a compound according to the invention may be formulated, optionally together with other active substances, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The compounds according to the invention may also be used in conjunction with other active substances, particularly for the treatment and/or prevention of the diseases and conditions mentioned above. Other active substances which are suitable for such combinations include for example those which potentiate the therapeutic effect of an SGLT antagonist according to the invention with respect to one of the indications mentioned and/or which allow the dosage of an SGLT antagonist according to the invention to be reduced. Therapeutic agents which are suitable for such a combination include, for example, antidiabetic agents such as metformin, sulphonylureas (e.g. glibenclamide, tolbutamide, glimepiride), nateglinide, repaglinide, thiazolidinediones (e.g. rosiglitazone, pioglitazone), PPAR-gamma-agonists (e.g. GI 262570) and antagonists, PPAR-gamma/alpha modulators (e.g. KRP 297), alpha-glucosidase inhibitors (e.g. acarbose, voglibose), DPPIV inhibitors (e.g. LAF237, MK-431), alpha2-antagonists, insulin and insulin analogues, GLP-1 and GLP-1 analogues (e.g. exendin-4) or amylin. The list also includes inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators or active substances for treating obesity, such as sibutramine or tetrahydrolipostatin, dexfenfluramine, axokine, antagonists of the cannabinoid1 receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramat, protein-kinase C inhibitors, advanced glycation end product inhibitors or aldose reductase inhibitors may be used for the treatment or prevention of complications of diabetes.

The dosage for the combination partners mentioned above is usefully 1/5 of the lowest dose normally recommended up to 1/1 of the normally recommended dose.

Therefore, in another aspect, this invention relates to the use of a compound according to the invention or a physiologically acceptable salt of such a compound combined with at least one of the active substances described above as a combination partner, for preparing a pharmaceutical composition which is suitable for the treatment or prevention of diseases or conditions which can be affected by inhibiting the sodium-dependent glucose cotransporter SGLT. These are preferably metabolic diseases, particularly one of the diseases or conditions listed above, most particularly diabetes or diabetic complications.

The use of the compound according to the invention, or a physiologically acceptable salt thereof, in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

Thus, for example, a pharmaceutical composition according to the invention comprises a combination of a compound according to the invention or a physiologically acceptable salt of such a compound and at least one angiotensin II receptor antagonist optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

In the foregoing and following text, H atoms of hydroxyl groups are not explicitly shown in every case in structural formulae. The Examples that follow are intended to illustrate the present invention without restricting it:

Preparation of the Starting Compounds:

EXAMPLE I

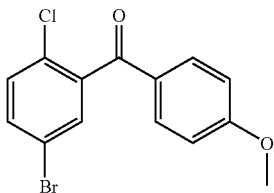

(5-Bromo-2-chloro-phenyl)-(4-methoxy-phenyl)-methanone 38.3 mL oxalyl chloride and 0.8 mL dimethylformamide are added to a mixture of 100 g 5-bromo-2-chloro-benzoic acid in 500 mL dichloromethane. The reaction mixture is stirred for 14 h, then filtered and separated from all volatile constituents in a rotary evaporator. The residue is dissolved in 150 mL dichloromethane, the resultant solution is cooled to −5° C., and 46.5 g anisole are added. Then 51.5 g aluminum trichloride are added batchwise so that the temperature does not exceed 5° C. The solution is stirred for 1 h at 1-5° C. and then poured onto crushed ice. The organic phase is separated off, and the aqueous phase is extracted with dichloromethane. The combined organic phases are washed with 1 M hydrochloric acid, twice with 1 M sodium hydroxide solution, and with brine. Then the organic phase is dried over sodium sulfate, the solvent is removed, and the residue is recrystallized from ethanol.

Yield: 86.3 g (64% of theory)

Mass spectrum (ESI$^+$): m/z=325/327/329 (Br+Cl) [M+H]$^+$

The following compounds may be obtained analogously to Example I:

(1) (5-bromo-2-methyl-phenyl)-(4-methoxy-phenyl)-methanone

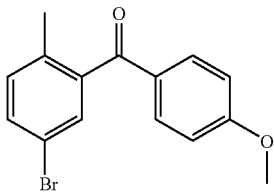

Mass spectrum (ESI$^+$): m/z=305/307 (Br) [M+H]$^+$ (2) (5-bromo-2-iodo-phenyl)-(4-ethoxy-phenyl)-methanone

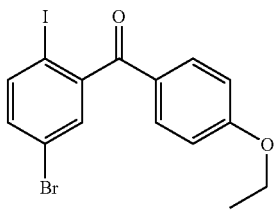

Mass spectrum (ESI$^+$): m/z=431/433 (Br) [M+H]$^+$

EXAMPLE II

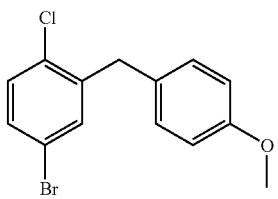

4-Bromo-1-chloro-2-(4-methoxy-benzyl)-benzene

A solution of 86.2 g (5-bromo-2-chloro-phenyl)-(4-methoxy-phenyl)-methanone and 101.5 mL triethylsilane in 75 mL dichloromethane and 150 mL acetonitrile is cooled to 10° C. Then with stirring 50.8 mL of boron trifluoride etherate are added so that the temperature does not exceed 20° C. The solution is stirred for 14 h at ambient temperature, before another 9 mL triethylsilane and 4.4 mL boron trifluoride etherate are added. The solution is stirred for a further 3 h period at 45-50° C. and then cooled to ambient temperature. A solution of 28 g potassium hydroxide in 70 mL water is added, and the resultant mixture is stirred for 2 h. The organic phase is separated and the aqueous phase is extracted another three times with diisopropylether. The combined organic phases are washed twice with 2 M potassium hydroxide solution and once with brine and then dried over sodium sulfate. After the solvent is evaporated, the residue is washed with ethanol and dried at 60° C.

Yield: 50.0 g (61% of theory)

Mass spectrum (ESI$^+$): m/z=310/312/314 (Br+Cl) [M+H]$^+$

The following compounds may be obtained analogously to Example II:

(1) 4-bromo-1-methyl-2-(4-methoxy-benzyl)-benzene

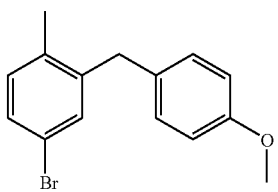

Mass spectrum (EI): m/z=290/292 (Br) [M]$^+$ (2) 4-bromo-1-iodo-2-(4-ethoxy-benzyl)-benzene

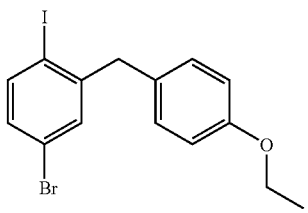

Mass spectrum (EI): m/z=434/436 (Br) [M+NH₄]⁺

EXAMPLE III

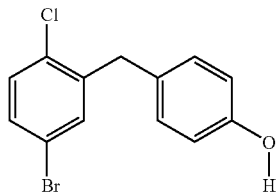

4-(5-bromo-2-chloro-benzyl)-phenol

A solution of 14.8 g 4-bromo-1-chloro-2-(4-methoxy-benzyl)-benzene in 150 mL dichloromethane is cooled in an ice bath. 50 mL of a 1 M solution of boron tribromide in dichloromethane are added, and the resulting solution is stirred for 2 h at ambient temperature. The solution is then cooled in an ice bath again, and saturated aqueous potassium carbonate solution is added dropwise. At ambient temperature the mixture is adjusted with aqueous 1 M hydrochloric acid to pH 1, the organic phase is separated off, and the aqueous phase is extracted three times with ethyl acetate. The combined organic phases are dried over sodium sulfate, and the solvent is removed completely.

Yield: 13.9 g (98% of theory)

Mass spectrum (ESI⁻): m/z =295/297/299 (Br+Cl) [M−H]⁻

The following compound may be obtained analogously to Example III:

(1) 4-(5-bromo-2-methyl-benzyl)-phenol

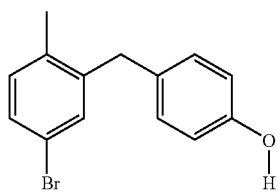

Mass spectrum (ESI): m/z=275/277 (Br) [M−H]⁻

EXAMPLE IV

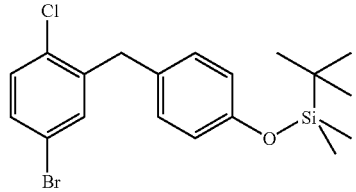

[4-(5-bromo-2-chloro-benzyl)-phenoxy]-tert-butyl-dimethyl-silane

A solution of 13.9 g 4-(5-bromo-2-chloro-benzyl)-phenol in 140 mL dichloromethane is cooled in an ice bath. Then 7.54 g tert-butyldimethylsilyl chloride in 20 mL dichloromethane are added followed by 9.8 mL triethylamine and 0.5 g 4-dimethylaminopyridine. The resultant solution is stirred for 16 h at ambient temperature and then diluted with 100 mL dichloromethane. The organic phase is washed twice with aqueous 1 M hydrochloric acid and once with aqueous sodium hydrogen carbonate solution and then dried over sodium sulfate. After the solvent is removed, the residue is filtered through silica gel (cyclohexane/ethyl acetate 100:1).

Yield: 16.8 g (87% of theory)

Mass spectrum (EI): m/z=410/412/414 (Br+Cl) [M]⁺

The following compound may be obtained analogously to Example IV:

(1) [4-(5-bromo-2-methyl-benzyl)-phenoxy]-tert-butyl-dimethyl-silane

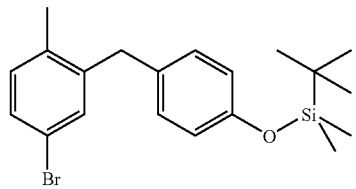

Mass spectrum (ESI⁺): m/z=391/393 (Br) [M+H]⁺

EXAMPLE V

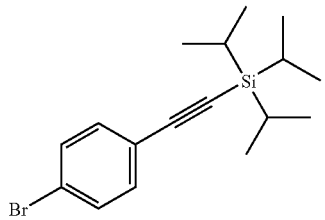

1-Bromo-4-triisopropylsilylethynyl-benzene 11.6 mL triisopropylsilylacetylen and 14.4 mL triethylamine followed by 0.2 g copper iodide and 0.73 g bis-(triphenylphosphine)-palladium dichloride are added under argon to an oxygen-free solution of 15.0 g 4-bromo-1-iodo-benzene in 150 mL dry tetrahydrofuran. The solution is stirred for 16 h at ambient temperature and then filtered through Celite and evaporated down. The residue is purified by chromatography on silica gel (cyclohexane).

Yield: 17.4 g (100% of theory)

Mass spectrum (ESI$^+$): m/z=336/338 (Br) [M]+

The following compound may be obtained analogously to Example V:

(1) [4-Bromo-2-(4-ethoxy-benzyl)-phenylethynyl]-triisopropyl-silane

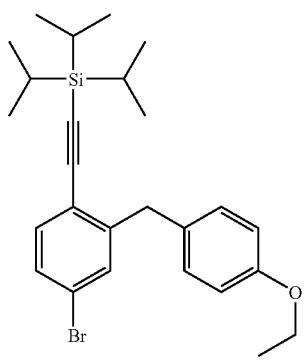

Mass spectrum (ESI$^+$): m/z=471/473 (Br) [M+H]$^+$

EXAMPLE VI

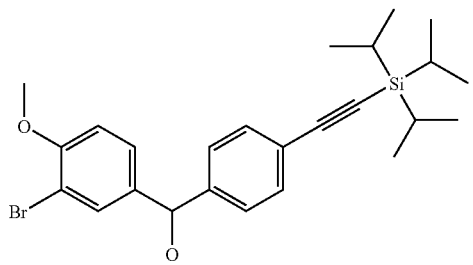

(3-Bromo-4-methoxy-phenyl)-{4-[(triisopropylsilyl)-ethynyl]-phenyl}-methanol 14.8 mL of a 1.6 M solution of n-butyllithium in hexane are added dropwise under argon to a solution of 8.0 g 1-bromo-4-triisopropylsilylethynyl-benzene in 80 mL dry tetrahydrofuran chilled to −78° C. The solution is stirred for 1 h at −70° C. Then 5.1 g 3-bromo-4-methoxy-benzaldehyde dissolved in 20 mL tetrahydrofuran are added dropwise over 15 min. The resulting solution is left in the cooling bath to warm to ambient temperature overnight. Then water is added and the mixture is extracted with ethyl acetate. The combined organic phases are dried over sodium sulfate and the solvent is removed. The residue is purified over silica gel (cyclohexane/ethyl acetate 9:1->1:1).

Yield: 8.1 g (72% of theory)

Mass spectrum (ESI$^-$): m/z=517/519 (Br) [M+HCOO]$^-$

EXAMPLE VII

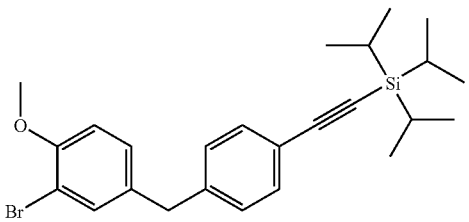

[4-(3-Bromo-4-methoxy-benzyl)-phenylethynyl]-triisopropyl-silane

A solution of 8.0 g (3-bromo-4-methoxy-phenyl)-{4-[(triisopropylsilyl)-ethynyl]-phenyl}-methanol and 5.7 mL triethylsilane in 80 mL dichloromethane is cooled in an ice bath. Then 6.5 mL trifluoroacetic acid are added dropwise, and the solution is stirred for 4 h in the cooling bath. The solution is diluted with dichloromethane and washed with aqueous sodium hydrogen carbonate solution. After drying over sodium sulfate the solvent is removed to give the product.

Yield: 7.6 g (93% of theory)

Mass spectrum (EI): m/z=456/458 (Br) [M$^-$]$^+$

EXAMPLE VIII

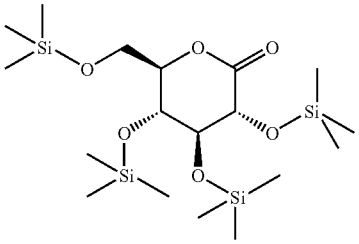

2.3.4.6-tetrakis-O-(trimethylsilyl)-D-glucopyranone

A solution of 20 g D-glucono-1,5-lactone and 98.5 mL N-methylmorpholine in 200 mL of tetrahydrofuran is cooled to −5° C. Then 85 mL trimethylsilyl chloride are added dropwise so that the temperature does not exceed 5° C. The solution is then stirred for 1 h at ambient temperature, 5 h at 35° C. and again for 14 h at ambient temperature. After the addition of 300 mL of toluene the solution is cooled in an ice bath, and 500 mL of water are added so that the temperature does not exceed 10° C. The organic phase is separated and washed with aqueous sodium dihydrogen phosphate solution, water and brine. The solvent is removed and the residue is azeotropically dried with toluene.

Yield: 52.5 g (approx. 90% pure)

Mass spectrum (ESI$^+$): m/z=467 [M+H]$^+$

EXAMPLE IX

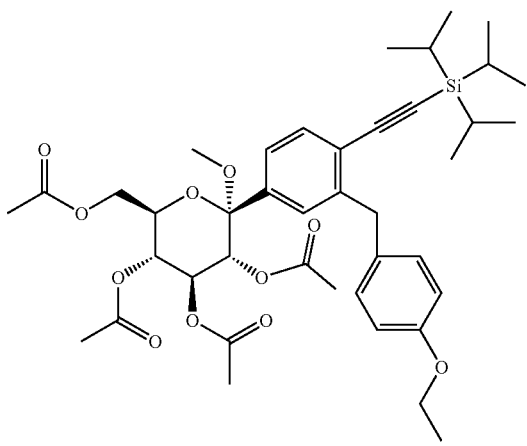

1-Triisopropylsilylethynyl-4-(1-methoxy-2,3,4,6-tetra-O-acetyl-D-glucopyranos-1-yl)-2-(4-ethoxy-benzyl)-benzene A solution of 1.6 g[4-bromo-2-(4-ethoxy-benzyl)-phenylethynyl]-triisopropyl-silane in 20 mL dry diethyl ether is cooled to −78° C. under argon atmosphere. 4.4 mL of a chilled (ca. −50° C.) 1.7 M solution of tert-butyllithium in pentane are added dropwise to the cooled solution. The resulting solution is stirred for 45 min at −78° C. and then a −78° C.-cold solution of 2.29 g of 2,3,4,6-tetrakis-O-(trimethylsilyl)-D-glucopyranone in 30 mL diethyl ether is added to the reaction solution through a transfer needle. The resulting solution is stirred for 3 h at −78° C. and then treated with a solution of 1.7 mL methanesulfonic acid in 50 mL of methanol. The cooling bath is removed and the solution is stirred for 16 h at ambient temperature. 3 mL ethyldiisopropylamine are added and the solvent is removed under reduced pressure. The residue is azeotropically dried with toluene and the dry residue is taken up in 50 mL toluene. 4.8 mL ethyidiisopropylamine are added and the resulting mixture is cooled in an ice bath. Then 2.4 mL acetic acid anhydride and 0.1 g 4-dimethylaminopyridine are added. The cooling bath is removed and the reaction solution is stirred at ambient temperature for 3 h. Aqueous sodium hydrogen carbonate solution is added and the resulting mixture is extracted with ethyl acetate. The combined organic extracts are washed with brine and dried over sodium sulfate. After removal of the solvent the residue is purified on silica gel (cyclohexane/ethyl acetate 4:1->1:2).

Yield: 1.5 g (59% of theory)

Mass spectrum (ESI$^+$): m/z=770 [M+NH$_4$]$^+$

EXAMPLE X

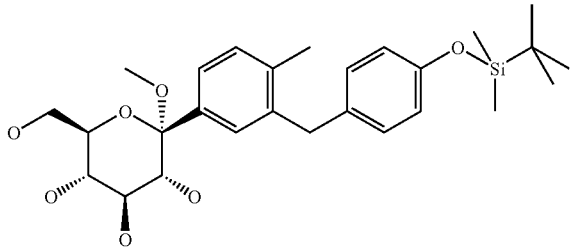

1-Methyl-4-(1-methoxy-D-glucopyranos-1-yl)-2-[4-(tert-butyl-dimethyl-silyloxy)-benzyl]-benzene A solution of 3.95 g [4-(5-bromo-2-methyl-benzyl)-phenoxy]-tert-butyl-dimethyl-silane in 40 mL dry diethyl ether is cooled to −78° C. under argon atmosphere. 13 mL of a chilled (ca. −50° C.) 1.7 M solution of tert-butyllithium in pentane are added dropwise to the cooled solution. The resulting solution is stirred for 45 min at −78° C. and then a −78° C.-cold solution of 6.8 g of 2,3,4,6-tetrakis-O-(trimethylsilyl)-D-glucopyranone in 30 mL diethyl ether is added to the reaction solution through a transfer needle. The resulting solution is stirred for 2 h at −78° C. and then treated with 100 mL of 1% acetic acid in water. The cooling bath is removed and 70 mL ethyl acetate are added. The organic phase is separated, washed with brine and dried over magnesium sulfate. After removing the solvent under reduced pressure the residue is taken up in 30 mL methanol and treated with 20 µl methanesulfonic acid. The solution is stirred at 40° C. for 20 min and then neutralised with ethyldiisopropylamine. The solvent is removed in vacuo and the residue is taken up in ethyl acetate. The resulting solution is washed with aqueous sodium hydrogen carbonate solution and dried over magnesium sulfate. After removal of the solvent the residue is purified over silica gel (dichloromethane/methanol 4:1->3:2).

Yield: 2.78 g (55% of theory)

Mass spectrum (ESI$^+$): m/z=522 [M+NH$_4$]$^+$

The following compound may be obtained analogously to Example X:

(1) 1-methoxy-2-(1-methoxy-D-glucopyranos-1-yl)-4-(4-triisopropylsilylethynyl-benzyl)-benzene

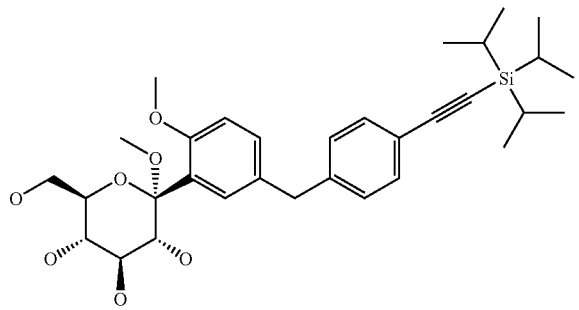

Mass spectrum (ESI$^+$): m/z=588 [M+NH$_4$]$^+$

EXAMPLE XI

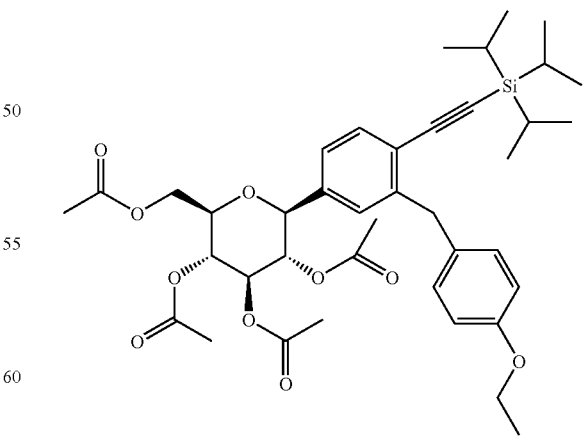

1-Triisopropylsilylethynyl-4-(2,3,4,6-tetra-O-acetyl-D-glucopyranos-1-yl)-2-(4-ethoxy-benzyl)-benzene To a solution of 0.37 g 1-triisopropylsilylethynyl-4-(1-methoxy-2,3,4,6-tetra-O-acetyl-D-glucopyranos1-yl)-2-(4- ethoxy-benzyl)-benzene and 0.45 mL triethylsilane in 3 mL acetonitrile are added 0.13 mL boron trifluoride etherate. The solution is stirred at room temperature for 5 h. Ethyl acetate is then added and the resultant solution is cooled in an ice bath. Aqueous sodium hydrogen carbonate solution is added to the chilled solution and the mixture is stirred for 10 min. The organic layer is separated and the aqueous layer is extracted with ethyl acetate. The combined organic layers are washed with brine and dried over magnesium sulfate. After removing the solvent the crude product is submitted to global deprotection without further purification.

EXAMPLE XII

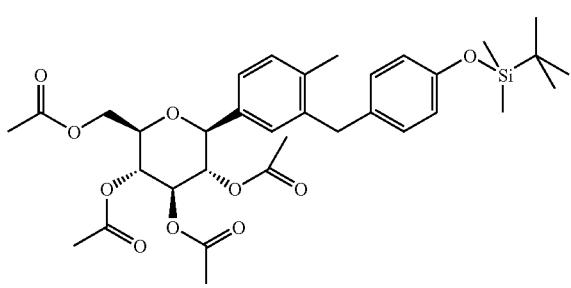

1-Methyl-4-(2,3,4,6-tetra-O-acetyl-β-D-glucopyranos-1-yl)-2-[4-(tert-butyl-dimethyl-silyloxy)-benzyl]-benzene A solution of 2.7 g 1-methyl-4-(1-methoxy-D-glucopyranos-1-yl)-2-[4-(tert-butyl-dimethyl-silyloxy)-benzyl]-benzene and 1.7 mL triethylsilane in 20 mL dichloromethane and 60 mL acetonitrile is cooled to −10° C. 1 mL boron trifluoride etherate is added dropwise to the cooled solution and the reaction solution is stirred at 0° C. for 0.5 h. The cooling bath is removed and the solution is stirred at ambient temperature for an additional 0.5 h. Aqueous sodium hydrogen carbonate solution is added and then the mixture is extracted with ethyl acetate. The combined extracts are washed with brine and dried over sodium sulfate. The solvent is removed in vacuo and the residue is dissolved in 20 mL dichloromethane. 4.3 mL pyridine, 4.8 mL acetic acid anhydride and 50 mg 4-dimethylaminopyridine are added and the resultant solution is stirred at room temperature for 1 h. Aqueous sodium hydrogen carbonate solution is added and the resultant mixture is stirred for an additional 30 min. The organic phase is separated and the aqueous phase is extracted with dichloromethane. The combined organic phases are washed with 1 M hydrochloric acid and aqueous sodium hydrogen carbonate solution and dried over sodium sulfate. After the solvent is removed the residue is chromatographed over silica gel (cyclohexane/ethyl acetate 2:1->1:2).

Yield: 1.5 g (44% of theory)
Mass spectrum (ESI$^+$): m/z=660 [M+NH$_4$]$^+$

The following compound may be obtained analogously to Example XII:

(1) 1-Methoxy-2-(2,3,4,6-tetra-O-acetyl-β-D-glucopyranos1-yl)-4-(4-triisopropylsilylethynyl-benzyl)-benzene

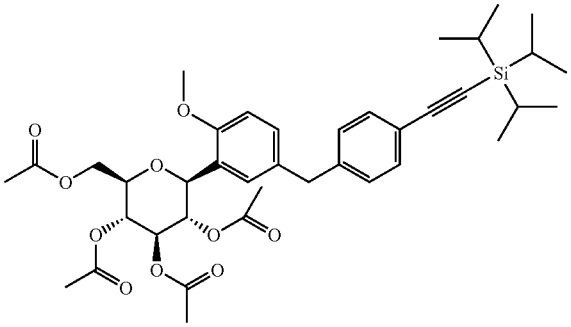

Mass spectrum (ESI$^+$): m/z=726 [M+NH$_4$]$^+$

EXAMPLE XIII

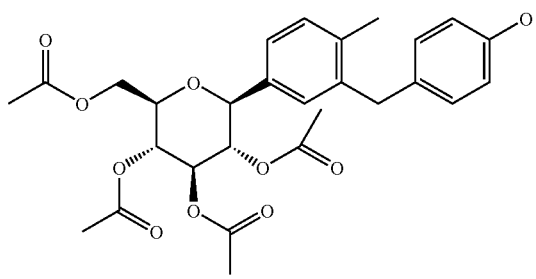

1-Methyl-4-(2,3,4,6-tetra-O-acetyl-β-D-glucopyranos-1-yl)-2-(4-hydroxy-benzyl)-benzene 2.02 mL of a 1 M solution of tetrabutylammonium fluoride in tetrahydrofuran are added to a solution of 1.3 g 1-methyl-4-(2,3,4,6-tetra-O-acetyl-β-D-glucopyranos1-yl)-2-[4-(tert-butyl-dimethyl-silyloxy)-benzyl]-benzene and 0.12 mL acetic acid in 10 mL of tetrahydrofuran. The solution is stirred for 30 min at ambient temperature, and then 50 mL ethyl acetate and 10 mL water are added. The organic layer is separated, washed with aqueous NaHCO$_3$ solution, and dried over MgSO$_4$. After removal of the solvent, the residue is recrystallized from a mixture of ethyl acetate and petrol ether.

Yield: 0.90 g (84% of theory)
Mass spectrum (ESI$^+$): m/z=546 [M+NH$_4$]$^+$

EXAMPLE XIII

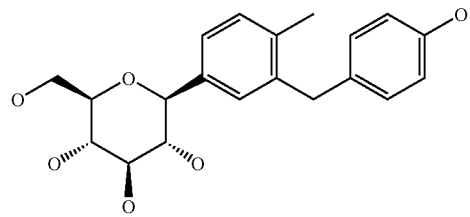

1-Methyl-4-(β-D-glucopyranos-1-yl)-2-(4-hydroxy-benzyl)-benzene

To a solution of 0.15 g 1-methoxy-2-(2,3,4,6-tetra-O-acetyl-β-D-glucopyranos1-yl)-4-(4-triisopropylsilylethynyl-benzyl)-benzene in 1 mL methanol is added 0.37 mL of 4 M sodium hydroxide solution. The reaction solution is stirred for 30 min at ambient temperature, then neutralised with 1 M hydrochloric acid and concentrated in vacuo. The residue is combined with brine and extracted with ethyl acetate. The combined organic extracts are dried over sodium sulfate and the solvent is evaporated under reduced pressure to give the desired product.

Yield: 0.90 g (44% of theory)
Mass spectrum (ESI$^+$): m/z=378 [M+NH$_4$]$^+$

EXAMPLE XIV

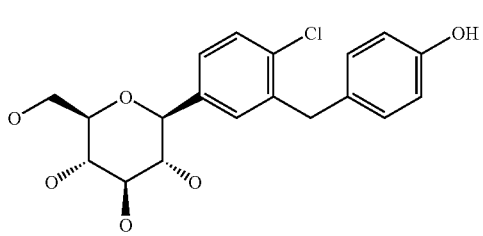

1-Chloro-4-(β-D-glucopyranos-1-yl)-2-(4-hydroxy-benzyl)-benzene

A solution of 4.0 g 1-methyl-4-(2,3,4,6-tetra-O-acetyl-β-D-glucopyranos1-yl)-2-(4-hydroxy-benzyl)-benzene in 42 mL dry diethyl ether is cooled to −80° C. under argon. 11.6 mL of a chilled (ca. −50° C.) 1.7 M solution of tert-butyl-lithium in pentane are slowly added to the cooled solution, and then the solution is stirred for 30 min at −80° C. This solution is then added dropwise through a transfer needle, which is cooled with dry ice, to a solution of 4.78 g 2,3,4,6-tetrakis-O-(trimethylsilyl)-D-glucopyranone in 38 mL diethyl ether chilled to −80° C. The resulting solution is stirred for 3 h at −78° C. Then a solution of 1.1 mL methanesulfonic acid in 35 mL methanol is added and the resultant reaction solution is stirred for another 16 h at ambient temperature. The solution is then neutralised with solid sodium hydrogen carbonate, ethyl acetate is added and the resultant solution is concentrated under reduced pressure. Aqueous sodium hydrogen carbonate solution is added to the remaining solution that is extracted four times with ethyl acetate. The combined organic phases are dried over sodium sulfate and the solvent is evaporated. The residue is dissolved in 30 mL acetonitrile and 30 mL dichloromethane and the resulting solution is cooled to −10° C. After the addition of 4.4 mL triethylsilane 2.6 mL boron trifluoride etherate are added dropwise so that the temperature does not exceed −5° C. After the addition is complete the reaction solution is stirred for another 5 h at −5 to −10° C. and then quenched by the addition of aqueous sodium hydrogen carbonate solution. The organic phase is separated and the aqueous phase is extracted four times with ethyl acetate. The combined organic phases are dried over sodium sulfate, the solvent is removed and the residue is purified by chromatography on silica gel (dichloromethane/methanol). The product then obtained is an approx. 6:1 mixture of β/α which can be converted into the pure β-anomer by global acetylation of the hydroxyl groups with acetic anhydride, pyridine and 4-dimethylaminopyridine in dichloromethane and recrystallisation of the acetylated product from ethanol. The pure acetylated β-product thus obtained is converted into the title compound by reacting in methanol with 4 M potassium hydroxide solution.

Yield: 1.6 g (46% of theory)
Mass spectrum (ESI$^+$): m/z=398/400 (Cl) (M+H)$^+$ The following compound may be obtained analogously to Example XII:

(1) 1-Methyl-4-(β-D-glucopyranos1-yl)-2-(4-hydroxy-benzyl)-benzene

Advantageously the reaction mixture obtained after the addition of the metalated aglycon to 2,3,4,6-tetrakis-O-(trimethylsilyl)-D-glucopyranone is quenched with 1% acetic acid in water and subsequently equilibrated to the more stable anomer as described in Example X.

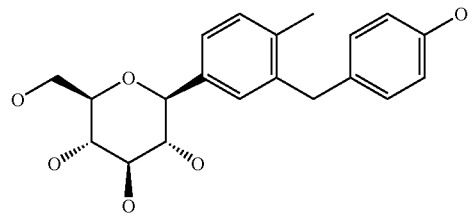

Mass spectrum (ESI$^+$): m/z=378 [M+NH$_4$]$^+$

EXAMPLE XV

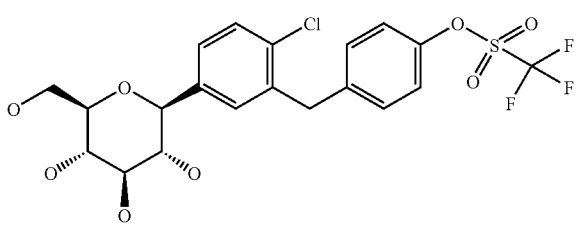

1-Chloro-4-(β-D-glucopyranos-1-yl)-2-[4-(trifluoromethylsulfonyloxy)-benzyl]-benzene 10 mg 4-dimethylaminopyridine are added to a solution of 0.38 g 1-chloro-4-(β-D-glucopyranos-1-yl)-2-(4-hydroxy-benzyl)-benzene, 0.21 mL triethylamine and 0.39 g N,N-bis-(trifluoromethanesulfonyl)-aniline in 10 mL dry dichloromethane. The solution is stirred for 4 h at ambient temperature and then combined with aqueous sodium chloride solution. The resulting mixture is extracted with ethyl acetate, the organic extracts are combined and dried over sodium sulfate, and the solvent is removed. The residue is purified by chromatography on silica gel (dichloromethane/methanol 1:0->4:1).

Yield: 0.33 g (64% of theory)
Mass spectrum (ESI$^+$): m/z=530/532 (Cl) [M+NH$_4$]$^+$

EXAMPLE XVI

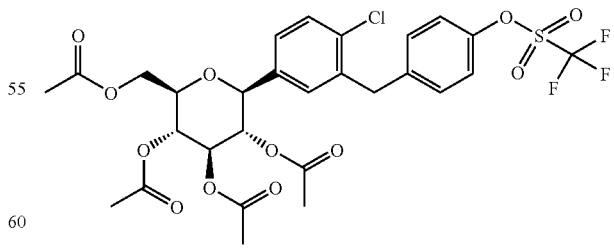

1-Chloro-4-(2,3,4,6-tetra-O-acetyl-β-D-glucopyranos-1-yl)-2-[4-(trifluoromethyisulfonyloxy)-benzyl]-benzene To a solution of 5.6 g 1-chloro-4-(β-D-glucopyranos-1-yl)-2-[4-(trifluoromethylsulfonyloxy)-benzyl]-benzene and 7 mL pyridine in 75 mL dichloromethane is added 7.8 mL acetic acid anhydride and 0.12 g 4-dimethylaminopyridine. The solution is stirred at ambient temperature for 1 h and then combined with 50 mL water. The organic phase is separated and the aqueous phase is extracted with dichloromethane. The combined organic phases are washed with 1 M hydrochloric acid and aqueous saturated sodium bicarbonate solution and dried over sodium sulfate. After evaporation of the solvent the product is yielded as a white solid.

Yield: 7.0 g (94% of theory)

Mass spectrum (ESI$^+$): m/z=698/700 (Cl) [M+NH$_4$]$^+$

EXAMPLE XVII

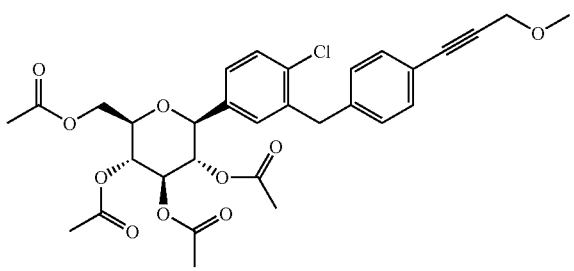

1-Chloro-4-(2,3,4,6-tetra-O-acetyl-β-D-glucopyranos-1-yl)-2-(4-methoxymethylethynyl-benzyl)-benzene 1 g 1-chloro-4-(2,3,4,6-tetra-O-acetyl-β-D-glucopyranos-1-yl)-2-[4-(trifluoromethylsulfonyloxy)-benzyl]-benzene, 2 mL triethylamine and 3 mL dimethylformamide are placed in a flask under argon atmosphere. 56 mg copper iodide, 103 mg bis-(triphenylphosphine)-palladium dichloride and finally 0.31 g methyl propargyl ether are added. The flask is tightly sealed and the mixture is stirred at 65° C. for 30 h. Then the reaction mixture is diluted with ethyl acetate and washed with 1 M hydrochloric acid. The organic phase is dried over magnesium sulfate and the solvent is removed under reduced pressure. The residue is chromatographed on silica gel (cyclohexane/ethyl acetate 4:1->2:1).

Yield: 0.13 g (15% of theory)

Mass spectrum (ESI$^+$): m/z=618/620 (Cl) [M+NH$_4$]$^+$

The following compounds may be obtained analogously to Example XVII:

(1) 1-Chloro-4-(2,3,4,6-tetra-O-acetyl-β-D-glucopyranos-1-yl)-2-(4-hydroxymethylethynyl-benzyl)-benzene

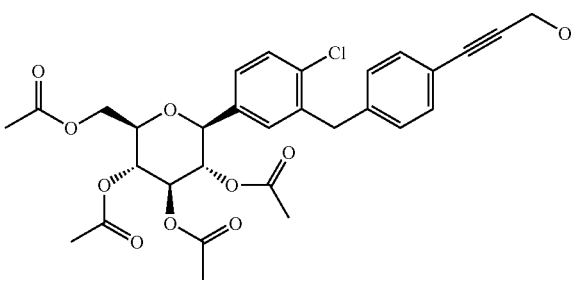

Mass spectrum (ESI$^+$): m/z=604/606 (Cl) [M+NH$_4$]$^+$ (2)-1-Chloro-4-(2,3,4,6-tetra-O-acetyl-β-D-glucopyranos1-yl)-2-(4-hydroxyethylethynyl-benzyl)-benzene

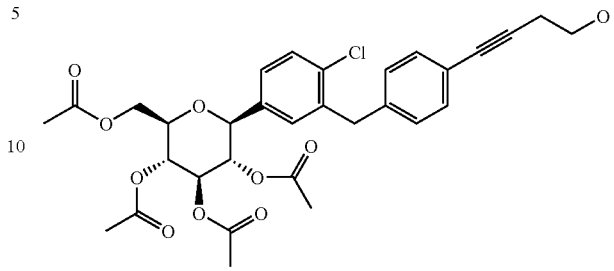

Mass spectrum (ESI$^+$): m/z=618/620 (Cl) [M+NH$_4$]$^+$

Preparation of the End Compounds:

EXAMPLE 1

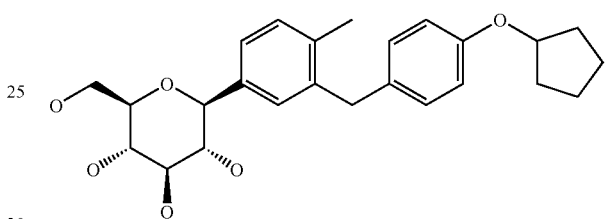

1-Methyl-2-(4-cyclopentyloxybenzyl)-4-(β-D-glucopyranos-1-yl)-benzene 0.17 mL iodocyclopentane are added to a mixture of 0.38 g 1-methyl-4-(β-D-glucopyranos-1-yl)-2-(4-hydroxybenzyl)-benzene and 0.53 g cesium carbonate in 4 mL dimethylformamide. The mixture is stirred at 65° C. for 4 h, before another 0.35 g cesium carbonate and 0.1 mL iodocyclopentane are added. After stirring the mixture for an additional 14 h at 45° C. brine is added and the resulting mixture is extracted with ethyl acetate. The combined organic phases are dried over sodium sulfate, the solvent is removed and the residue is purified by chromatography on silica gel (dichloromethane/methanol 1:0->8:1).

Yield: 0.29 g (63% of theory)

Mass spectrum (ESI$^+$): m/z=446 [M+NH$_4$]$^+$

The following compounds may be obtained analogously to Example 1:

(2) 1-Methyl-2-[4-((R)-tetrahydrofuran-3-yloxy)-benzyl]-4-(β3-D-glucopyranos-1-yl)-benzene The reaction is carried out with tetrahydrofuran-3-yl (S)-toluene-4-sulfonate as the coupling partner.

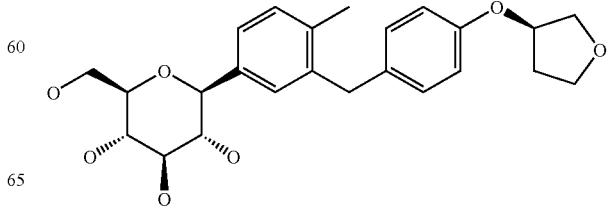

Mass spectrum (ESI$^+$): m/z=448 [M+NH$_4$]$^+$

(3) 1-Methyl-2-[4-((S)-tetrahydrofuran-3-yloxy)-benzyl]-4-(β-D-glucopyranos1-yl)-benzene The reaction is carried out with tetrahydrofuran-3-yl (R)-toluene-4-sulphonate as the coupling partner.

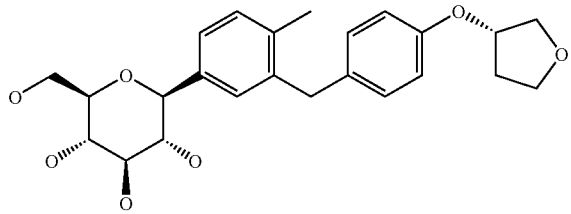

Mass spectrum (ESI⁺): m/z=431 [M+H]⁺

(4) 1-Methyl-2-(4-cyclohexyloxy-benzyl)-4-(β-D-glucopyranos-1-yl)-benzene

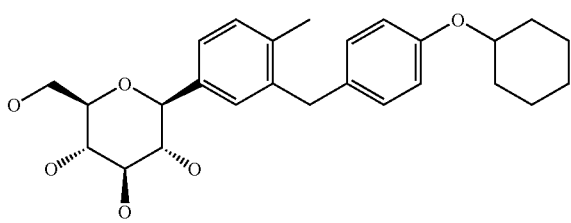

(5) 1-Chloro-2-[4-(1-tert-butyloxycarbonylpiperidin-4-yloxy)-benzyl]-4-(β-D-glucopyranos-1-yl)-benzene The reaction is carried out with 1-tert-butyloxycarbonyl-4-methylsulfonyloxy-piperidine as the electrophile.

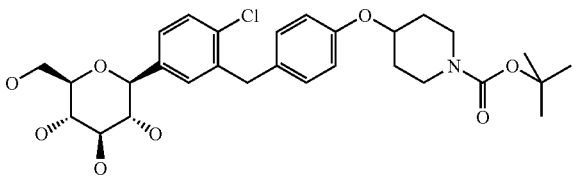

Mass spectrum (ESI⁺): m/z=586/588 (Cl) [M+Na]⁺

EXAMPLE 6

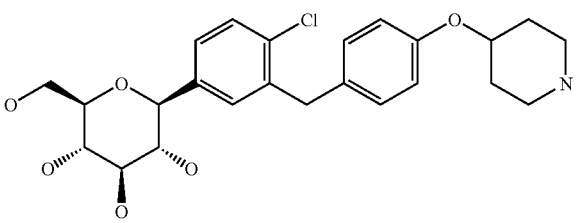

1-Chloro-2-[4-(piperdin-4-yloxy)-benzyl]-4-(β-D-glucopyranos-1-yl)-benzene 2 mL trifluoroacetic acid are added to a solution of 0.19 g 1-chloro-4-(β-D-glucopyranos-1-yl)-2-[4-(1-tert-butyloxycarbonylpiperidin-4-yloxy)-benzyl]-benzene in 4 mL dichloromethane. The solution is stirred for 1.5 h at ambient temperature and then diluted with ethyl acetate. The resulting solution is treated with aqueous potassium carbonate solution and the organic phase is separated. The remaining basic aqueous phase is extracted with ethyl acetate and the combined organic phases are dried over sodium sulfate. The solvent is removed under reduced pressure to yield the product.

Yield: 0.060 g (38% of theory)
Mass spectrum (ESI⁺): m/z=464/466 (Cl) [M+H]⁺

EXAMPLE 7

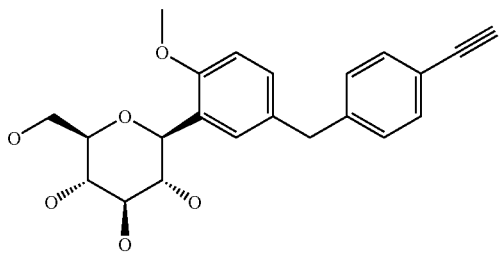

1-Methoxy-2-(β-D-glucopyranos-1-yl)-4-(4-ethynyl-benzyl)-benzene 0.78 mL of a 1 M solution of tetrabutylammonium fluoride in tetrahydrofuran are added to a solution of 0.55 g 1-methoxy-2-(2,3,4,6-tetra-O-acetyl-β-D-glucopyranos-1-yl)-4-(4-triisopropylsilylethynyl-benzyl)-benzene in 2 mL tetrahydrofuran. The solution is stirred for 30 min at ambient temperature and then diluted with 4 mL methanol. 0.85 mL of 4 M potassium hydroxide solution are added and the resulting solution is stirred for an additional 30 min at ambient temperature. The reaction solution is neutralized with 1 M hydrochloric acid and concentrated in vacuo. The residue is combined with brine and extracted with ethyl acetate. The combined organic extracts are dried over sodium sulfate and the solvent is evaporated. The residue is chromatographed over silica gel (dichloromethane/methanol 9:1->2:1).

Yield: 0.18 g (60% of theory)
Mass spectrum (ESI⁺): m/z=402 [M+NH₄]⁺

EXAMPLE 8

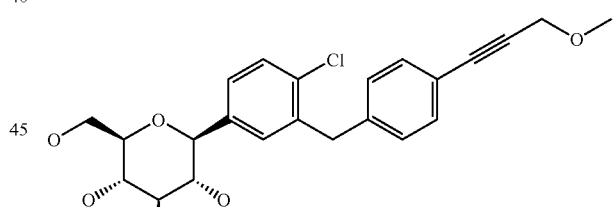

1-Chloro-2-(4-methoxymethylethynyl-benzyl)-4-(β-D-glucopyranos-1-yl)-benzene

To a solution of 0.11 g 1-chloro-4-(2,3,4,6-tetra-O-acetyl-β-D-glucopyranos1-yl)-2-(4-methoxymethylethynyl-benzyl)-benzene in 2 mL methanol is added 0.85 mL of 1 M aqueous potassium hydroxide solution. The solution is stirred for 1 h at ambient temperature and then diluted with ethyl acetate. The resulting solution is washed with brine and dried over sodium sulfate. The solvent is evaporated and the residue is filtered through silica gel (dichloromethane/methanol 9:1->2:1).

Yield: 0.075 g (95% of theory)
Mass spectrum (ESI⁺): m/z=450/452 [M+NH₄]⁺

The following compounds may be obtained analogously to Example 8:

(9) 1-Chloro-2-(4-hydroxymethylethynyl-benzyl)-4-(β-D-glucopyranos-1-yl)-benzene

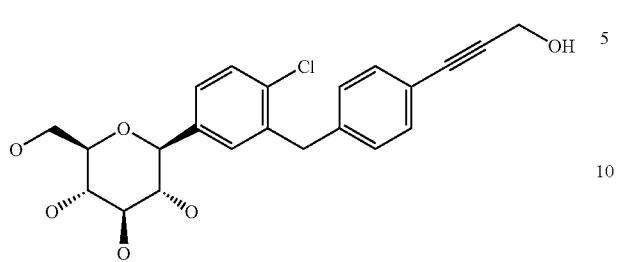

Mass spectrum (ESI$^+$): m/z=436/438 (Cl) [M+NH$_4$]$^+$

(10) 1-Chloro-2-(4-hydroxyethylethynyl-benzyl)-4-(β-D-glucopyranos-1-yl)-benzene

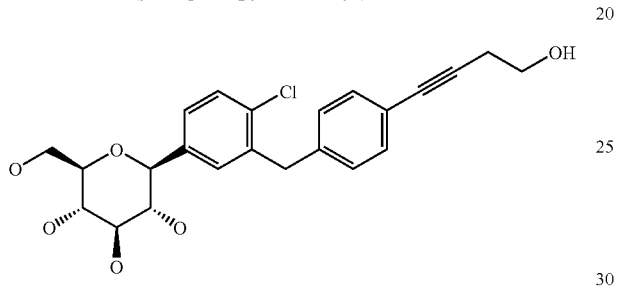

Mass spectrum (ESI$^+$): m/z=450/452 (Cl) [M+NH$_4$]$^+$

The following compounds are also prepared analogously to the above-mentioned Examples or other methods known from the literature:

(11) 1-Ethynyl-2-(4-methoxy-benzyl)-4-(β-D-glucopyranos1-yl)-benzene

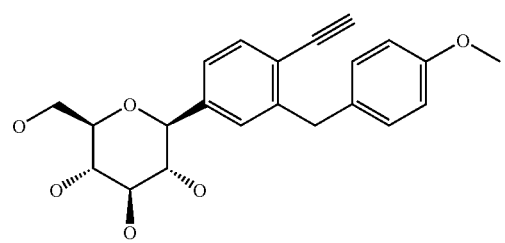

(12) 1-Methyl-2-(4-butyn1-yl-benzyl)-4-(β-D-glucopyranos-1-yl)-benzene

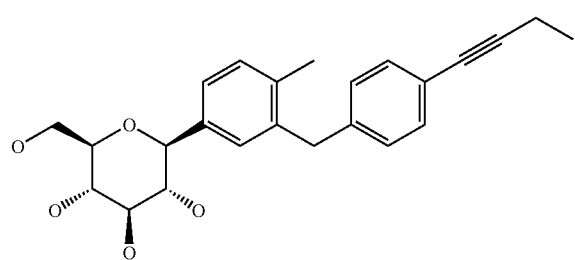

(13) 1-Chloro-2-(4-propyn1-yl-benzyl)-4-(β-D-glucopyranos1-yl)-benzene

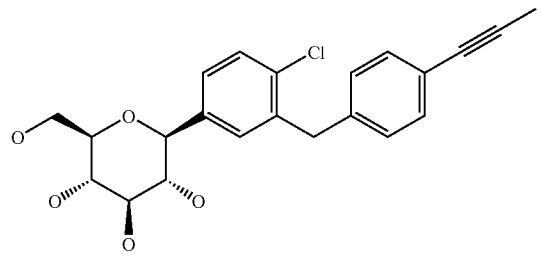

(14) 1-Methyl-2-(4-propyn1-yl-benzyl)-4-(β-D-glucopyranos-1-yl)-benzene

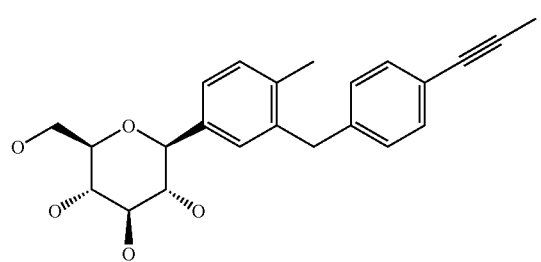

(15) 1-Isopropyl-2-(4-ethynyl-benzyl)-4-(β-D-glucopyranos1-yl)-benzene

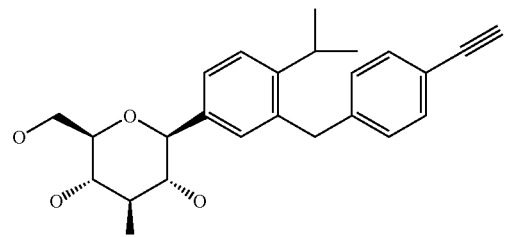

(16) 1-Chloro-2-(4-isopropylethynyl-benzyl)-4-(β-D-glucopyranos-1-yl)-benzene

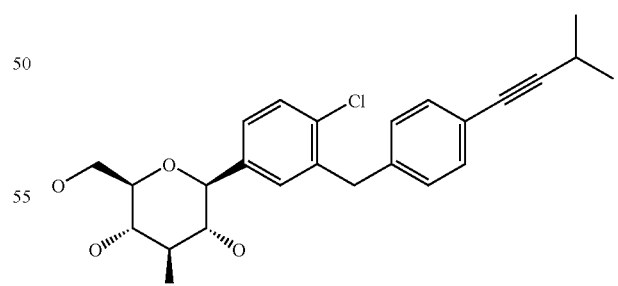

Some examples of formulations will now be described in which the term "active substance" denotes one or more compounds according to the invention, including the prodrugs or salts thereof. In the case of one of the combinations with one or additional active substances as described previously, the term "active substance" also includes the additional active substances.

EXAMPLE A

Tablets Containing 100 mg of Active Substance

Composition:

| 1 tablet contains: | |
| --- | --- |
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg
Diameter: 10 mm, biplanar, facetted on both sides and notched on one side.

EXAMPLE B

Tablets Containing 150 mg of Active Substance

Composition:

| 1 tablet contains: | |
| --- | --- |
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg
die: 10 mm, flat

EXAMPLE C

Hard Gelatine Capsules Containing 150 mg of Active Substance

Composition:

| 1 capsule contains: | | |
| --- | --- | --- |
| active substance | | 150.0 mg |
| corn starch (dried) | approx. | 180.0 mg |
| lactose (powdered) | approx. | 87.0 mg |
| magnesium stearate | | 3.0 mg |
| | approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg
Capsule shell: size 1 hard gelatine capsule.

EXAMPLE D

Suppositories Containing 150 mg of Active Substance

Composition:

| 1 suppository contains: | |
| --- | --- |
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE E

Ampoules Containing 10 mg Active Substance

Composition:

| active substance | | 10.0 mg |
| --- | --- | --- |
| 0.01N hydrochloric acid q.s. | | |
| double-distilled water | ad | 2.0 ml |

Preparation:

The active substance is dissolved in the necessary amount of 0.01 N HCl, made isotonic with common salt, filtered sterile and transferred into 2 ml ampoules.

EXAMPLE F

Ampoules Containing 50 mg of Active Substance

Composition:

| active substance | | 50.0 mg |
| --- | --- | --- |
| 0.01N hydrochloric acid q.s. | | |
| double-distilled water | ad | 10.0 ml |

Preparation:

The active substance is dissolved in the necessary amount of 0.01 N HCl, made isotonic with common salt, filtered sterile and transferred into 10 ml ampoules.

The invention claimed is:

1. A glucopyranosyl-substituted benzene derivative selected from among:
   (1) 1-Methyl-2-(4-cyclopentyloxy-benzyl)-4-(β-D-glucopyranos-1-yl)-benzene,
   (2) 1-Methyl-2-[4-((R)-tetrahydrofuran-3-yloxy)-benzyl]-4-(β-D-glucopyranos-1-yl)-benzene,
   (3) 1-Methyl-2-[4-((S)-tetrahydrofuran-3-yloxy)-benzyl]-4-(β-D-glucopyranos-1-yl)-benzene,
   (4) 1-Methyl-2-(4-cyclohexyloxy-benzyl)-4-(β-D-glucopyranos-1-yl)-benzene,
   (5) 1-Chloro-2-[4-(1-tert-butyloxycarbonylpiperidin-4-yloxy)-benzyl]-4-(β-D-glucopyranos-1-yl)-benzene,
   (6) 1-Chloro-2-[4-(piperdin-4-yloxy)-benzyl]-4-(β-D-glucopyranos-1-yl)-benzene,
   (7) 1-Methoxy-2-(β-D-glucopyranos-1-yl)-4-(4-ethynylbenzyl)-benzene,
   (8) 1-Chloro-2-(4-methoxymethylethynyl-benzyl)-4-(β-D-glucopyranos-1-yl)-benzene,
   (9) 1-Chloro-2-(4-hydroxymethylethynyl-benzyl)-4-(β-D-glucopyranos-1-yl)-benzene,
   (10) 1-Chloro-2-(4-hydroxyethylethynyl-benzyl)-4-(β-D-glucopyranos-1-yl)-benzene,
   (11) 1-Ethynyl-2-(4-methoxy-benzyl)-4-(β-D-glucopyranos-1-yl)-benzene,
   (12) 1-Methyl-2-(4-butyn-1-yl-benzyl)-4-(β-D-glucopyranos-1-yl)-benzene,
   (13) 1-Chloro-2-(4-propyn-1-yl-benzyl)-4-(β-D-glucopyranos-1-yl)-benzene,
   (14) 1-Methyl-2-(4-propyn-1-yl-benzyl)-4-(β-D-glucopyranos-1-yl)-benzene,
   (15) 1-Isopropyl-2-(4-ethynyl-benzyl)-4-(β-D-glucopyranos-1-yl)-benzene,
   (16) 1-Chloro-2-(4-isopropylethynyl-benzyl)-4-(β-D-glucopyranos-1-yl)-benzene,
   or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl, or a pharmaceutically acceptable salt thereof;
   including the tautomers, the stereoisomers thereof or the mixtures thereof, and salts thereof.

2. A glucopyranosyl-substituted benzene derivative according to claim 1 wherein the hydrogen atom of the hydroxyl group O-6 of the β-D-glucopyranosyl-group is replaced by a group selected from among ($C_{1-8}$-alkyl)carbonyl, ($C_{1-8}$-alkyl) oxycarbonyl and phenylcarbonyl, or a pharmaceutically acceptable salt thereof.

3. A physiologically acceptable salt of the compounds according to claim 1 with inorganic or organic acids.

4. A pharmaceutical composition comprised of a compound according to claim 1 optionally together with one or more inert carriers and/or diluents.

5. A pharmaceutical composition comprised of a compound according to claim 1 or a physiologically acceptable salt thereof.

6. A method of treating conditions which can be influenced by inhibiting the sodium-dependent glucose cotransporter SGLT, said method comprised of the steps of administering to a patient in need thereof a therapeutically effective amount of a compound according to claim 1 or a physiologically acceptable salt thereof, wherein said conditions is selected from the group consisting of type 1 and type 2 diabetes mellitus, complications of diabetes, metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

7. A method of treating metabolic disorders said method comprised of the steps of administering to a patient in need thereof a therapeutically effective amount of a compound according to claim 1 or a physiologically acceptable salt thereof, wherein the metabolic disorder is selected from the group consisting of type 1 and type 2 diabetes mellitus, complications of diabetes, metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

8. A method of treating the degeneration of pancreatic beta cells and/or for improving the functionality of beta cells, said method comprised of the step of administering to a patient in need thereof a therapeutically effective amount of a compound according to claim 1 or a physiologically acceptable salt thereof.

* * * * *